(12) United States Patent
Suhadolnik

(10) Patent No.: US 6,214,554 B1
(45) Date of Patent: Apr. 10, 2001

(54) CHRONIC FATIGUE SYNDROME DIAGNOSIS

(75) Inventor: Robert J. Suhadolnik, Roslyn, PA (US)

(73) Assignee: Temple University of the Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 09/296,211

(22) Filed: Apr. 21, 1999

Related U.S. Application Data

(60) Division of application No. 08/895,120, filed on Jul. 16, 1997, now Pat. No. 5,985,565, which is a continuation-in-part of application No. 08/728,109, filed on Oct. 9, 1996, now abandoned.

(51) Int. Cl.[7] .................................................... C12Q 1/68

(52) U.S. Cl. .................................................. 435/6; 435/18

(58) Field of Search ................................. 435/6, 18, 7.4, 435/7.92; 530/350; 536/28.1

(56) References Cited

U.S. PATENT DOCUMENTS

| | | | |
|---|---|---|---|
| 4,990,498 | * 2/1991 | Suhadolnik | 514/47 |
| 5,258,369 | 11/1993 | Carter | 514/44 |
| 5,776,690 | 7/1998 | Vojdani et al. | 435/6 |
| 5,985,565 | * 11/1999 | Suhadolnik | 435/6 |

FOREIGN PATENT DOCUMENTS

| | | |
|---|---|---|
| 0 306 347 A2 | 3/1989 | (EP) . |
| 0 325 018 | 7/1989 | (EP) . |
| 0 525 917 A2 | 2/1993 | (EP) . |
| 0 285 263 B1 | 6/1994 | (EP) . |
| WO 91/00097 | 1/1991 | (WO) . |

OTHER PUBLICATIONS

Suhadolnik, et al., Proceedings, First World Congress on Chronic Fatigue Syndrome and Related Disorders, "Further Evidence for Biochemical Defects in the 2–5A Synthetase/RNase L and PKR Pathways In Chronic Fatigue Syndrome", p. 69, Nov. 9, 1995.
Kon et al., *The Journal of Biological Chemistry* 271 (33):19983–19990 (Aug. 16, 1996).
Suhadolnik et al., *Clinical Infectious Diseases* 18 (1):S96–S104 (Jan. 1994).
Suhadolnik et al., *Biochemistry* 27:8840–8846 (1988).
Suhadolnik et al., *In Vivo* 8:599–604 (1994).
Salehzada T., Regeneration of Enzyme Activity After Western Blot: Activation of Rnase L by Z–5A on Filter–Importance for its Detection,*Anal Biochemistry* 196:410–414 (1991).

* cited by examiner

*Primary Examiner*—Ralph Gitomer
(74) *Attorney, Agent, or Firm*—Seidel, Gonda, Lavorgna & Monaco PC

(57) ABSTRACT

Chronic fatigue syndrome is diagnosed through detection of an about 30 kDa RNase L molecule under native conditions in cellular extracts of RNase L-containing cells such as peripheral blood mononuclear cells. Proteins are fractionated according to molecular weight under nondenaturing conditions. The fractionated proteins are assayed for the presence of the about 30 kDa protein having 2-5A-dependent RNase L enzyme activity. The severity of the affliction may be determined by testing for the presence of RNase L molecules having approximate molecular weights of 30 and 80 kDa. The presence of the about 30 kDa RNase L, and the absence of the about 80 kDa RNase L molecule, correlates with severe chronic fatigue syndrome. The presence of both RNase L molecules indicates a less severe chronic fatigue syndrome affliction. Under denaturing conditions, and in the presence of protease inhibitors, chronic fatigue syndrome may be diagnosed through the detection of an about 37 kDa 2-5A binding protein.

17 Claims, 3 Drawing Sheets

CFS                    Control
1   2                  3   4
+   -                  +   -
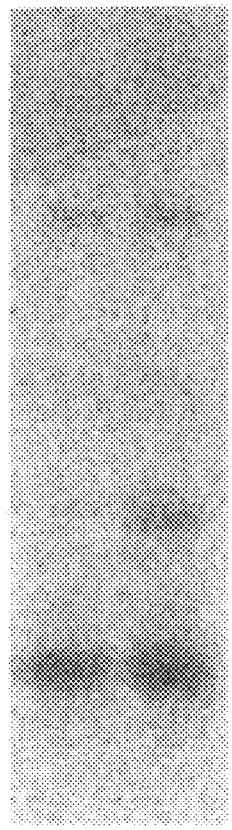   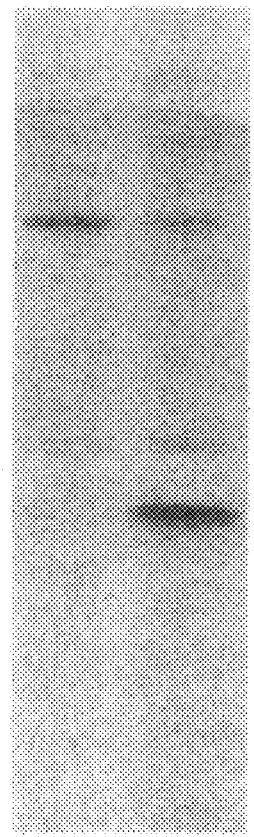
← 80 kDa →
← 42 kDa →
← 37 kDa →
FIG. 3

CHRONIC FATIGUE SYNDROME DIAGNOSIS

CROSS-REFERENCE TO RELATED APPLICATION

This application is a divisional application of Ser. No. 08/895,120 filed Jul. 16, 1997 now U.S. Pat. No. 5,985,565, which is a continuation in part of Ser. No. 08/728,109 filed Oct. 9, 1996, now abandoned.

REFERENCE TO GOVERNMENT GRANT

The invention described herein was made in the course of work supported by U.S. Public Health Service grant R21 AI38378. The United States government has certain rights in the invention.

FIELD OF THE INVENTION

This invention relates to the diagnosis of chronic fatigue syndrome (CFS) through detection of a unique molecular marker associated with the disease.

BACKGROUND OF THE INVENTION

Chronic fatigue syndrome (CFS) is an illness of unknown etiology, often associated with sudden onset, flu-like symptoms, debilitating fatigue, low-grade fever, myalgia and neurocognitive dysfunction. CFS patients typically display reduced Karnofsky performance scores (KPS). The Karnofsky performance test measures an individual's ability to function and carry on normal activities. Karnofsky scores range form zero for a nonfunctional or dead patient to 100 for a completely normal function. Diagnosis of CFS remains one of exclusion.

An accumulating body of evidence suggests that CFS is associated with disregulation of both humoral and cellular immunity, including mitogen response, reactivation of viruses, abnormal cytokine production, diminished natural killer cell function and changes in intermediary metabolites. It has been suggested that the clinical and immunological abnormalities observed in CFS might include defects in the double-stranded RNA (dsRNA)-dependent, interferon-inducible pathways, i.e., the 2',5'-oligoadenylate (2-5A) synthetase/RNase L and p68 kinase (PKR) antiviral defense pathways (Suhadolnik et al., *Clin. Infect. Dis.* 18:S96–S104, 1994; Suhadolnik et al., In Vivo 8:599–604 (1994). The 2-5A synthetase/RNase L pathway is part of the antiviral defense mechanism in mammalian cells; this pathway also has a role in the regulation of cell growth and differentiation (Lengyel, *Ann. Review Biochem.* 51:251–282, 1982; Sen et al., *Adv. Virus Res.* 42:57–102, 1993).

When activated by dsRNA, 2-5A synthetase converts ATP to 2',5'-linked oligoadenylates with 5'-terminal phosphates. Biologically active 2-5A binds to and activates a latent endoribonuclease, RNase L, which hydrolyzes single-stranded viral and cellular RNA, primarily after UpNp sequences, thereby inhibiting protein synthesis.

Previous studies on the 2-5A synthetase/RNase L pathway in CFS revealed a statistically significant dysregulation in which the 2-5A synthetase is present predominantly in its activated form, bioactive 2-5A levels are elevated, and RNase L activity is upregulated (Suhadolnik et al., *Clin. Infect. Dis.*, supra; Suhadolnik et al., In Vivo, supra). Expression of the serine-threonine kinase, PKR, is down-regulated in CFS (Suhadolnik et al., In Vivo, supra). PKR controls initiation of protein translation through phosphorylation of eIF-2.

Despite these efforts, a clear cut molecular marker for CFS has not been identified. What is needed is a biochemical test, relying on an unambiguous molecular marker for CFS, which may form the basis of a definitive CFS diagnosis.

ABBREVIATIONS

The following abbreviations may be used herein:

| | |
|---|---|
| AMP: | adenosine 5'-monophosphate; |
| 2-Azido-AMP: | 2-azidoadenosine 5'-monophosphate; |
| 8-Azido-AMP: | 8-azidoadenosine 5'-monophosphate; |
| 2,8-Azido-AMP: | 2,8-diazidoadenosine 5'-monophosphate; |
| 2-5A: | 2',5'-oligoadenylate, that is, an oligomer of adenylic acid with (2'→5')-phosphodiester linkages and 5'-triphosphate; |
| CFS: | chronic fatigue syndrome; |
| dsRNA: | double-stranded RNA; |
| ELISA: | enzyme-linked immunosorbent assay; |
| etheno-AMP | $N^1N^6$-ethenoadenosine 5'-monophosphate; |
| GST: | glutathione S-transferase; |
| HEPES: | 4-(2-hydroxyethyl)-piperazine ethanesulfonic acid; |
| PBMC: | peripheral blood mononuclear cells; |
| PBS: | phosphate-buffered saline |
| $p_3A_3$ | trimer of adenylic acid with (2'→5')-phosphodiester linkages and 5'-triphosphate; |
| pApAp(8-azidoA): | 5'-O-phosphoryl-adenylyl-(2'→5')-adenylyl-(2'→5')-8-azidoadenosine; |
| poly(U)-3'-pCp: | polyuridylic acid having a cytosine residue attached to the 3' terminus thereof; |
| SDS-PAGE: | sodium dodecylsulfate-polyacrylamide gel electrophoresis. |

SUMMARY OF THE INVENTION

A method for diagnosing chronic fatigue syndrome comprises assaying a patient sample for the presence of an about 30 kDa RNase L.

According to one embodiment, the method comprises (a) fractionating the proteins in the patient sample according to molecular weight under nondenaturing conditions, and (b) assaying the fractionated proteins for an about 30 kDa protein having RNase L activity. The RNase L activity assay may comprise, for example, detecting formation of specific cleavage products (SCP) from hydrolysis of 28S and/or 18S RNA, or detecting the hydrolysis of poly(U)-3'-pCp.

According to another embodiment, the invention includes a method for diagnosing chronic fatigue syndrome comprising:

(a) contacting a patient sample prepared in the presence of added protease inhibitor with a probe comprising a compound according to formula I bearing a detectable label, under conditions sufficient to form covalent conjugates of said labeled probe compound and 2',5'-oligoadenylate-binding proteins in the sample:

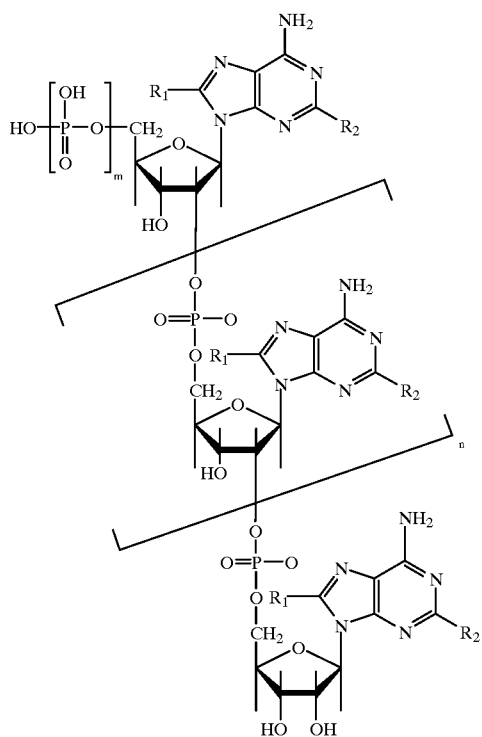

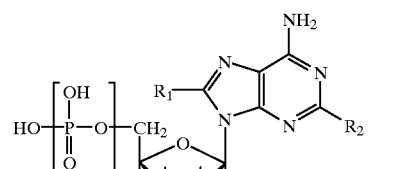

wherein
　m is an integer from 0 to 3,
　n is an integer from 1 to 3, and
　each $R_1$ and each $R_2$ is, independently of each other $R_1$ and $R_2$, hydrogen or $N_3$, provided at least one $R_1$ or $R_2$ is $N_3$,
or a water soluble salt of said compound;

(b) contacting the sample containing said covalent conjugates with an antibody which binds RNase L species in the sample;

(c) separating the proteins in said sample by gel electrophoresis; and (d) examining said separated proteins for marker proteins which
　(i) have formed a covalent conjugate with the labeled probe compound, and
　(ii) are bound by said antibody;

the presence of a marker protein of about 37 kDa apparent molecular weight according to sodium dodecyl sulfate-polyacrylamide gel electrophoresis being diagnostic for chronic fatigue syndrome.

According to yet another embodiment, the invention includes a method for detecting severe chronic fatigue syndrome comprising:

(a) contacting a patient sample with a probe comprising a compound according to formula I bearing a detectable label, under conditions sufficient to form covalent conjugates of said labeled probe and 2',5'-oligoadenylate-binding proteins in the sample:

wherein
　m is an integer from 0 to 3,
　n is an integer from 1 to 3, and
　each $R_1$ and each $R_2$ is, independently of each other $R_1$ and $R_2$, hydrogen or $N_3$, provided at least one $R_1$ or $R_2$ is $N_3$,
or a water soluble salt of said compound;

(b) contacting the sample containing said covalent conjugates with an antibody which binds RNase L species in the sample;

(c) separating the proteins in said sample by gel electrophoresis; and (d) examining said separated proteins for marker proteins which
　(i) have formed a covalent conjugate with the labeled probe compound, and
　(ii) are bound by said antibody;

the presence of a marker protein of about 37 kDa apparent molecular weight according to sodium dodecyl sulfate-polyacrylamide gel electrophoresis, and the absence of a marker protein of about 80 kDa apparent molecular weight according to sodium dodecyl sulfate-polyacrylamide gel electrophoresis, being diagnostic for severe chronic fatigue syndrome.

According to a further embodiment of the invention, a method for assessing the relative severity of chronic fatigue syndrome is provided comprising assaying a patient sample under native conditions for the presence of RNase L molecules having molecular weights of about 30 and about 80 kDa. The presence of an about 30 kDa RNase L molecule, and the absence of an about 80 kDa RNase L molecule, indicates severe chronic fatigue syndrome. The presence of RNase L molecules of both molecular weights indicates less severe chronic fatigue syndrome. The assay may be conducted by (a) fractionating the proteins in the patient sample according to molecular weight under nondenaturing conditions; and (b) assaying the fractionated proteins for about 30 kDa and about 80 kDa proteins having RNase L activity.

BRIEF DESCRIPTION OF THE DRAWINGS

FIGS. 2D, 2E and 2F show the results of the analytical gel permeation HPLC fractionation of PBMC extracts from the same healthy (FIG. 2D) and CFS (FIGS. 2E and 2F) individuals as FIGS. 2A, 2B and 2C, this time under native (non-denaturing) conditions, followed by RNase L activity assay of the fractions. Aliquots of each fraction were assayed in the presence of $p_3A_3$ with poly(U)-3'-[$^{32}$P]pCp. No 2-5A binding or 2-5A dependent RNase L enzyme activity was detected in fractions 0–150. Molecular weight markers are indicated by arrows. The healthy control PBMC extract (FIGS. 2A and 2D) is also shown in FIG. 1, lane 2. The CFS PBMC extract of FIGS. 2B and 2E, is also described in FIG. 1, lane 1. The CFS PBMC extract of FIGS. 2D and 2E, is also shown in FIG. 1, lane 8.

FIG. 3 shows the fractionation (10% SDS-PAGE) of proteins collected from PBMC extracts (100 μg protein) prepared in the presence (+) or absence (−) of protease inhibitors, photoaffinity labeled with the 2-5A photoprobe, [$^{32}$P]pApAp(8-azidoA), and immunoprecipitated with polyclonal antibody to recombinant, human 80 kDa RNase L. The photoaffinity labeled, immunoreactive 2-5A binding proteins were separated by 10% SDS-PAGE and quantitated by phosphorimaging. Molecular masses of the 2-5A binding proteins are indicated. Lanes 1,2: CFS PBMC extracts; lanes 3,4: healthy control PBMC extracts.

DETAILED DESCRIPTION OF THE INVENTION

Figure 1:
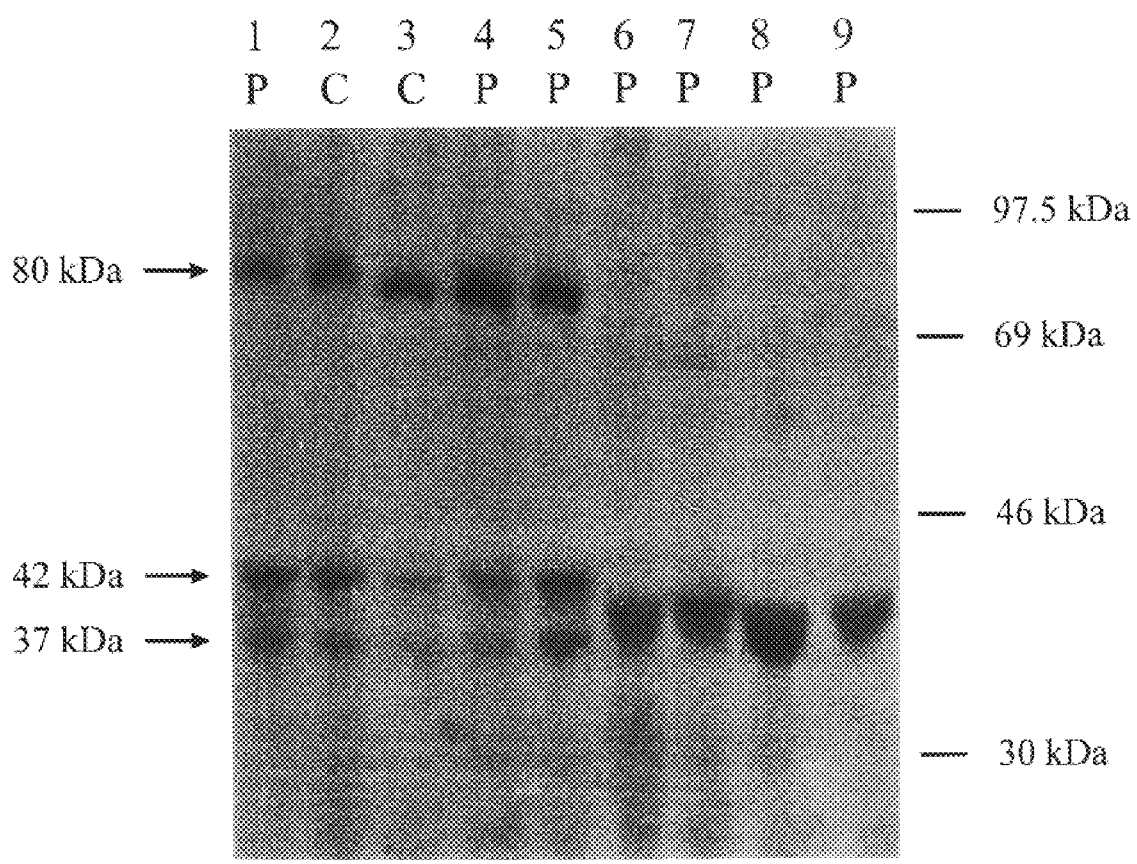
FIG. 1 shows the fractionation (10% SDS-PAGE) and autoradiography of Protein A-Sepharose bound proteins collected from peripheral blood mononuclear cell (PBMC) extracts which were incubated with the 2-5A photoprobe, [$^{32}$P]pApAp(8-azidoA), UV irradiated and incubated with polyclonal antibody to recombinant, human RNase L. P=patient; C=control. Lanes 1, 4–9: individuals with CFS; lanes 2,3: representative healthy controls. RNase L activities as determined in ribosomal RNA cleavage assays: 79, 54, 37, 73, 59, 253, 127,>500 and 253, for lanes 1–9, respectively.

Biologically active 2-5A binds to and activates the latent endoribonuclease, RNase L. Activated RNase L in turn hydrolyzes single-stranded viral and cellular RNA, thereby inhibiting protein synthesis. It has been determined that cell extracts from healthy individuals contain an about 80 kDa 2-5A binding protein with 2-5A-dependent RNase L activity. The extracts may also contain a 42 kDa 2-5A binding protein with 2-5A-dependent RNase L activity. CFS patients, on the other hand, have been demonstrated to possess a distinct 30 kDA 2-5A binding protein having 2-5A-dependent RNase L activity. By "RNase L activity" is meant the enzymatic activity of RNase L in hydrolyzing its RNA substrates.

PBMC of one subset of CFS patients examined contained 2-5A binding proteins with 2-5A-dependent RNase L enzyme activity at molecular weights of about 80 and about 30 kDa. In the absence of added protease inhibitor in the preparation of the patient cell extracts, a 2-5A binding protein with 2-5A-dependent RNase L activity at a molecular weight of about 42 kDa was also observed. The presence of the about 80 kDa species coincided with less aggressive CFS. PBMC of another subset of CFS patients contained 2-5A binding activity and 2-5A-dependent RNase L enzyme activity only at about 30 kDa. This profile coincided with a more aggressive CFS. Regardless of the severity of the disease state, CFS-afflicted individuals may be identified by the presence of the about 30 kDa RNase L species, which is always absent in individuals not afflicted with CFS. Detection of the unique and heretofore unknown about 30 kDa RNase L species under native conditions permits, for the first time, an accurate and unequivocal biochemical test for CFS. Similarly, detection of an about 37 kDa species under non-native conditions correlates with CFS.

According to the present invention, samples are taken from individuals suspected of CFS affliction and assayed for the presence of the about 30 kDa 2-5A-dependent RNase L. The sample may be taken from any suitable RNase L-containing cells. Blood or a fraction thereof, such as serum or plasma, may also be employed. RNase L is present in substantial concentrations in mononuclear cells. Thus, a preferred cellular source for samples comprises PBMC. The sample may be prepared by collecting cells by centrifugation, disrupting the cells, and removing the cell debris to obtain a cell-free extract. The extract is then examined for the presence of the about 30 kDa RNase L.

According to one embodiment of the invention, PBMC is separated from heparinized blood by Ficoll-Hypaque density gradient centrifugation, and cytoplasmic extracts are prepared, according to the procedures of Suhadolnik et al., *Biochemistry* 22:4153–4158 (1983). To avoid loss of RNase L activity, preparation of the cytoplasmic extracts should be commenced within about two hours of blood collection. Briefly, heparinized whole blood is diluted 1:1 with PBS. Two volumes of diluted blood are overlayered on 1 volume of Ficoll-Hypaque (Boyum, Scand. *J. Clin. Lab. Invest.* 97:1–109, 1968) at a density of 1.080 and centrifuged at 20° C., for 30 minutes at 1000 g. The PBMC layer is removed and washed once with 5 volumes of PBS. Isolated PBMC are resuspended in 5 mL of red blood cell lysing buffer (155 mM $NH_4Cl$, 10 mM $NaHCO_3$, pH 7.4, 0.1 mM EDTA), kept on ice for 5 min, and washed twice with PBS. The isolated PBMC are resuspended in 0.1 or 0.2 ml (approximately 10 times cell volume) of a buffer (20 mM HEPES, pH 7.5, 5 mM $MgCl_2$, 120 mM KCl, 10% glycerol, 1 mM dithiothreitol) containing 0.5% NONIDET P40 and kept on ice 10 minutes to lyse the cells. Cytoplasmic extracts are obtained by centrifugation for 6 minutes at 8000 g and 25° C. Cell-free extracts may be stored indefinitely at −70° C. in either 25- or 50-μL aliquots.

A protease inhibitor may be optionally added to the cytoplasmic extract, e.g. Mini-Complete™ protease inhibitor cocktail tablets (Boehringer/Mannheim), according to the manufacturer's directions. Mini-Complete™ inhibitor contains aprotinin, leupeptin, pefabloc® SC and EDTA. The expression "added protease inhibitor" as used herein in connection with the preparation of cell extracts for diagnostic testing means exogenously added protease inhibitor, beyond the protease inhibitor which may naturally occur in the cell extract. When an extract is said to "be prepared in the presence of added protease inhibitor," what is meant is an amount of protease inhibitor which is sufficient to substantially completely inhibit the activity of proteases present in the extract.

The cell-free extract is then assayed for the presence of the about 30 kDa CFS RNase L. By "about" with reference to the molecular weight of various RNase L forms is meant a molecule having the indicated molecular weight within the range of plus or minus 1 kDa. Cell extracts are fractionated according to molecular weight under native, nondenaturing conditions. The about 30 kDa fraction is then assayed for 2-5A-dependent RNase L activity in the presence of 2-5A or analog thereof capable of binding to and activating RNase L in the fraction. By "native conditions" is meant fractionation by a process which substantially preserves the activity of RNase L species in the sample. Essentially, native conditions are conditions which do not denature proteins, most particularly, conditions which do not denature enzymes. Nondenaturing conditions for fractionating proteins according to molecular weight are well-known to those skilled in the art. Nondenaturing fractionation of proteins according to molecular weight is most advantageously carried out by gel filtration high performance liquid chromatography. One column chromatography material for this purpose is SUPERDEX 200 from Pharmacia LKB Biotechnology, Piscataway, N.J. This material is effective in fractionating proteins having molecular weights in the range of 15 kDa to 200 kDa.

The 2-5A-dependent RNase L activity of the about 30 kDa molecular weight fraction may be determined by a number of different RNase L assays. The RNase L activity assay may take the form of a core-cellulose assay (Silverman et al. *Anal. Biochem.* 144:450460, 1985, incorporated herein by reference), which involves immobilizing and partial purifying of 2-5A binding molecules on 2-5A core-cellulose, and measuring RNase L activity in the sample by conversion of poly(U)[$^{32}$P]pCp to acid-soluble fragments.

Alternatively, 2-5A-dependent RNase L activity may be detected by a ribosomal RNA cleavage assay, and detection of highly characteristic specific cleavage products (SCPs) (Suhadolnik et al., *Clin. Infect. Dis.*, supra, incorporated herein by reference). Accordingly, the samples are incubated with cytoplasmic extracts (140 μg of protein per assay) of an RNase L-deficient subclone of L929 cells (the source of intact 28S and 18S ribosomal RNA) at 30° C. for 60 minutes. Total RNA is extracted, denatured and analyzed by electrophoresis on 1.8% agarose gels. After ethidium bromide staining, RNA bands are visualized under ultraviolet light. The formation of SCPs due to RNase L activity may be quantitated by densitometric tracings of gel photographs and expressed as the ratio of the products of the reaction (SCPs) to the substrate (28S and 18S rRNA) remaining at the end of the incubation period. For a discussion of SCPs see Wreschner et al., Nature 289:414–417 (1981), the entire disclosure of which is incorporated herein by reference.

According to yet another method, the 2-5A-dependent RNase L activity of the about 30 kDa molecular weight fraction may be determined by assaying the hydrolysis of a suitably labeled RNase L substrate, such as a radiolabeled substrate. For example, RNase L activity in a protein fraction may be determined by contacting the fraction with the substrate poly(U)-3'-[$^{32}$P]pCp in the presence of $p_3A_3$, followed by a radioactivity assay by scintillation spectrometry.

In addition to detection of the about 30 kDa RNase L, the same methodology may be utilized to assay for the presence of the about 80 kDa species which is present in the cells of normal individuals. The presence of the about 30 kDa RNase L molecule, and the absence of the about 80 kDa RNase L molecule, indicates that the patient is afflicted with severe or advanced CFS. The presence of RNase L molecules of both molecular weights in the patient sample is indicative of less severe or less advanced CFS affliction. The patients severely disabled from CFS, whose cell extracts contain only the 30 kDa RNase L, and not the 80 kDa 2-5A molecule, are generally characterized by Karnofsky performance scores (KPS) of 60 or lower. These patients also lack the about 42 kDa RNase L species which may be observed in healthy controls and in CFS patients with less severe disease. The CFS patients whose cell extracts contain both the about 30 kDa and about 80 kDa RNase L species are generally characterized by a KPS of 60.

As an alternative to fractionation according to molecular weight, the proteins of the patient sample may be partially purified by conventional methods using salts such as ammonium sulfate and solvents such as acetone or butyl alcohol, followed by diethylaminoethyl-cellulose chromatography. This methodology results in protein separation on the basis of charge. The 30 and 80 kDa forms of RNase L may be separated by this method based upon total charge differences.

According to another embodiment of the invention, which may be used to identify patients with severe CFS, cell extracts are photoaffinity labeled with a photoprobe comprising a 2-5A azido analog, followed by immunoprecipitation with RNase L antibody and molecular weight fractionation. This methodology specifically identifies 2-5A binding, RNase L immunoreactive proteins, and eliminates proteins which immunoreact with the RNase L antibody, but which are not 2-5A binding proteins. The methodology also eliminates 2-5A binding proteins which are not immunoreactive with the antibody.

Photolabeling/immunoprecipitation/fractionation of cell extracts of healthy individuals prepared in the absence of added protease inhibitor, and photolabelling/immunoprecipitation/fractionation of cell extracts of CFS patients with less severe symptoms, detects 2-5A binding proteins with approximate molecular masses of 80 and 37 kDa in SDS-PAGE. In the absence of added protease inhibitor, a 2-5A binding protein with an approximate molecular mass of about 42 kDa is also detected. For patients with severe CFS symptoms, the methodology detects the about 37 kDa 2-5A binding protein. The about 80 kDa 2-5A binding protein is not observed. No about 42 kDa protein is observed either, even in the absence of added protease inhibitor. When cell extracts of healthy individuals are prepared in the presence of added protease inhibitor, the about 37 kDa and the about 42 kDa 2-5A binding proteins are not observed upon photolabeling/immunoprecipitation/fractionation of cell extracts.

Accordingly photolabeling/immunoprecipitation/fractionation methodology may be utilized to detect the absence of the about 80 kDa 2-5A binding protein to thereby identify patients with severe CFS, bearing in mind that the assay can not be used to distinguish between healthy individuals and CFS patients with less severe CFS symptoms, where the cell extracts are prepared without added protease inhibitor. When cell extracts are prepared from healthy individuals in the presence of added protease inhibitor, the about 37 kDa 2-5A binding protein is not observed. On the other hand, the 37 kDa molecule is observed in CFS patient extracts prepared in the presence of protease inhibitor. The herein photolabeling/immunoprecipitation/fractionation methodology can thus be used to distinguish CFS from normal cell extracts, provided that the extracts are prepared in the presence of added protease inhibitor.

It should be appreciated that while the foregoing photolabelling/immunoprecipitation/fractionation method may detect an about 37 kDa 2-5A binding protein in cell extracts of healthy individuals prepared in the absence of added protease inhibitor, the detected molecule lacks 2-5A-dependent RNase L activity in healthy individuals.

Figure 2:
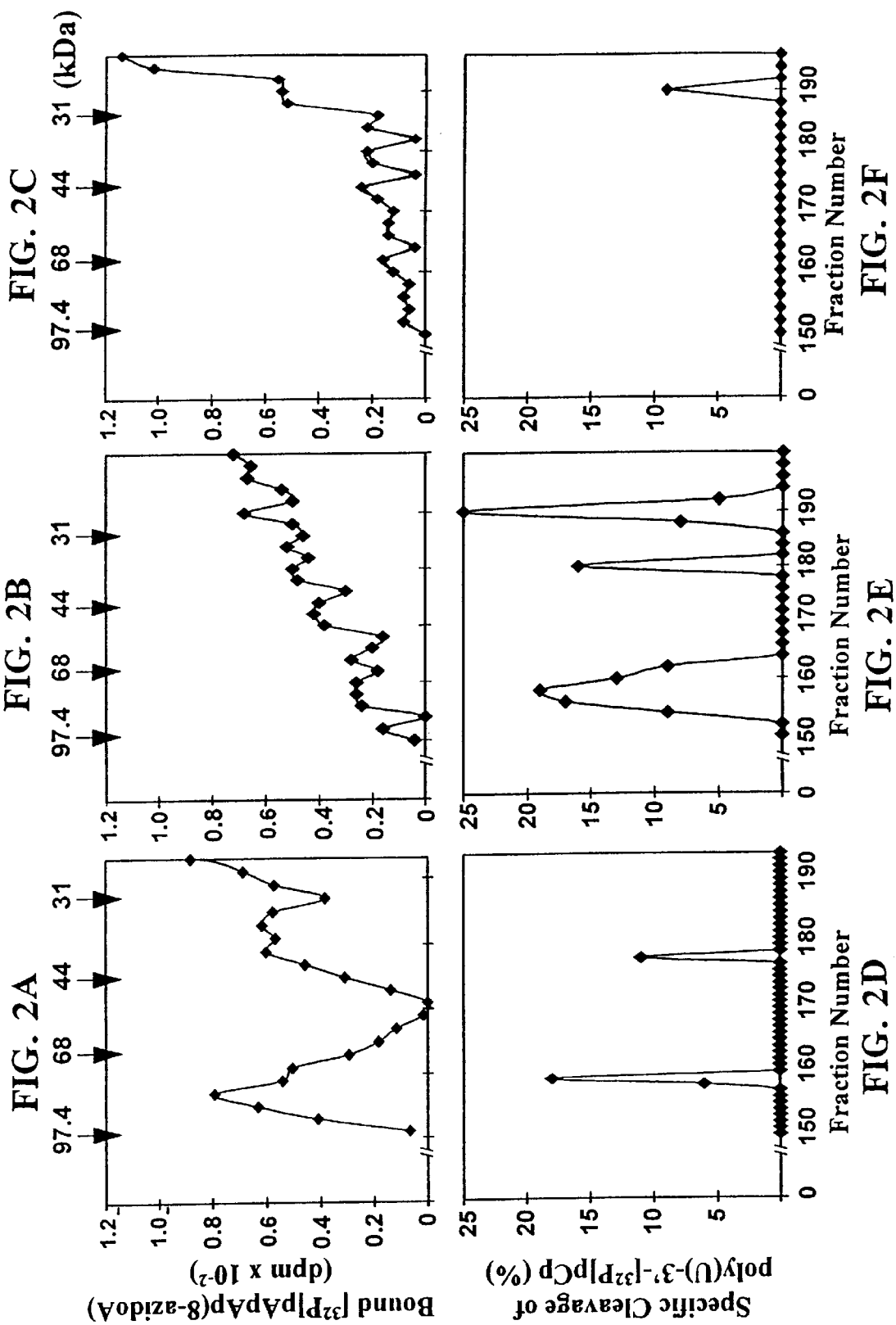
FIGS. 2A–2F show the results of the analytical gel permeation HPLC fractionation of PBMC extracts from healthy (FIG. 2A) and CFS (FIGS. 2A and 2C) individuals under native (non-denaturing) conditions. The extracts were photolabeled with [$^{32}$P]pApAp(8-azidoA) prior to fractionation. Aliquots of the fractions collected from each PBMC extract were assayed for radioactivity by scintillation spectrometry.

The photoprobe used in the photolabeling/immunoprecipitation/-fractionation assay comprises an analog of 2-5A according to formula I, above, wherein either or both of the 2- or 8-hydrogens of one or more of the 2-5A molecule's adenine residues are replaced by an azido group. Photolabeling of 2-5A binding proteins in cell extracts comprises contacting the extract with labelled photoprobe (e.g., radiolabeled) under conditions sufficient to form covalent conjugates of the photoprobe and 2-5A binding proteins. Generally, this is accomplished by incubation of a mixture of the extract and the photoprobe under low intensity ultraviolet light. The preparation of the 2-5A azido analogs for use as photoprobes is described in U.S. Pat. No. 4,990,498 (enzymatic synthesis) and Charubala et al., Helv. Chim. Acta 72:1354–1361 (1989) (chemical synthesis). The entire disclosures of both documents are incorporated herein by reference. The 2-5A azido analogs effectively bind to and activate RNase L. By virtue of the photosensitive azido group, the 2-5A azido analogs readily form reactive nitrene radical intermediates (C-N) upon 5 exposure to low intensity ultraviolet light. The nitrene radical intermediate reacts with, and covalently photolabels, biological molecules. The in situ photoactivation of the 2-5A azido analogs following binding to RNase L does not interfere with RNase L activity (See U.S. Pat. No. 4,990,498, FIG. 2).

The 2-5A azido analog according to formula I may comprise an oligomer of a single azido-AMP species (e.g., 2-azido-AMP), as in the case of 2-azidoadenylyl-(2'→5')2-azidoadenylyl-(2'→5')2-azidoadenosine; an oligomer of both 2-azido-AMP and 8-azido-AMP, as in the case of 2-azidoadenylyl-((2'→5')8-azidoadenylyl-(2'→5')2-azidoadenosine; an oligomer of AMP and 2-azido-AMP or 8-azido-AMP, as in the case of 2-azidoadenylyl-(2'→5')2-azidoadenylyl-(2'→5')2-azidoadenosine; or an oligomer resulting from any combination of any of the monomers AMP, 2-azido-AMP, 8-azido-AMP, or 2,8-azido-AMP, provided at least one of such monomer is an azido-AMP species.

The 2-5A azido analog of formula I, for use in the practice of the present invention, is preferably a trimer (n=1). The preferred degree of 5'-phosphorylation is monophosphorylation (m=1). Particularly preferred are oligomers containing one or more 8-azidoadenylyl residues, particularly 2-5A azido analogs wherein the 2'-terminal nucleotide is 8-azidoadenosine, e.g., 5'-O-phosphoryl-adenylyl-(2'→5')-adenylyl-(2'→5')-8-azidoadenosine.

The 2-5A azido analog preferably bears a detectable label, permitting its identification. The label may comprise, for example, a radiolabel, such as $^{32}P$, $^{3}H$, $^{14}C$ or $^{15}N$. $^{32}P$ is the strongest β-particle emitter and is therefore preferred. Alternatively, the label may comprise one or more incorporated etheno groups, which strongly fluoresce. The amino group on carbon-6 of one or more of the adenine nuclei may be converted to etheno groups to form $N^{1}N^{6}$-ethenoadenine, or the fluorescent oligomer may be synthesized de novo from etheno-AMP, or from a combination of etheno-AMP, azido AMP monomer and AMP monomers, provided at least one monomer comprises etheno-AMP. See Suhadolnik et al., J. Biol. Chem. 252:4125–4133 (1977), the entire disclosure of which is incorporated herein by reference. Other labels for detecting biological molecules are known to those skilled in the art.

Following photolabeling with the 2-5A azido analogue, the cell extract is then combined with RNase L polyclonal antibody. The antibody for the immunoprecipitation step may comprise polyclonal antisera raised against human recombinant 80 kDa, which antisera also recognizes the about 30 kDa CFS RNase L. Recombinant human 80 kDa RNase L may be expressed by standard recombinant techniques from the known full-length cDNA (Zhou et al., Cell 72:753–765, 1993, incorporated herein by reference; GenBank sequence, accession number L10381, incorporated herein by reference). Polyclonal antisera against the recombinant human 80 kDa RNase L is obtained by immunizing animals with the recombinant protein and harvesting the antisera, through known techniques.

The RNase L antibody may comprise an intact antibody, or fragments thereof capable of binding antigen, including but not necessarily limited to, Fab and F (ab')$_2$ fragments. Hence, as used herein, the term "antibody" includes intact antibody molecules and fragments thereof which retain antigen binding ability. A labeled secondary antibody may be optionally employed to aid in the identification of antigen-antibody complexes formed by the RNase L antibody. The secondary antibody is capable of binding to RNase L, or to the primary RNase L antibody. The labelled secondary antibody may comprise, for example, sheep-, goat-, or mouse anti-rabbit IgG, in the case where the primary RNase L antibody is a rabbit antibody.

The label on the secondary antibody is detected by physical or chemical means. Such labels include radiolabels; chromophoric labels such as fluorescent, ultraviolet-absorbing or light absorbing labels; and enzyme labels. Any appropriate radioisotope may be used as the label, for example $^{125}I$, $^{131}I$, $^{3}H$, and $^{14}C$. In an ELISA, the label is an enzyme, e.g. alkaline phosphatase, which cleaves a chromogenic substrate to release a chromophoric cleavage product. In the case of alkaline phosphatase, the substrate may comprise, for example, phenolphthalein monophosphate or p-nitrophenylphosphate.

Following immunoprecipitation, the complexes comprising antibody, photoprobe and 2-5A binding protein formed in the extract are then purified by absorption by Protein A-resin (e.g., Protein-A agarose), followed by washing and elution of proteins from the resin. The eluted protein mixture is fractionated by gel electrophoresis and the photolabeled/immunoprecipitated 2-5A binding proteins are visualized by detection of the label carried on the photoprobe or antibody. The molecular weights of the labeled bands are determined by reference to known molecular weight standards.

The practice of the invention is illustrated by the following non-limiting examples. All CFS patient PBMC extracts tested under nondenaturing conditions were characterized by the presence of the about 30 kDa RNase L, and all healthy controls lacked this low molecular weight RNase L. Thus, the about 30 kDa RNase L is a molecular marker for CFS affliction. The data presented herein also indicate that, in addition to being characterized by the presence of the about 30 kDa RNase L marker, the severest cases of CFS are characterized by an absence of the about 80 kDa RNase L species. The CFS patients with less severe symptoms retained the about 80 kDa RNase L species as well as the 30 kDA species. Thus, based upon the data obtained, the pattern of occurrence of the 80 and 30 kDa RNase L molecules correlates with the severity of CFS clinical presentation.

Similar results were achieved with azido-photolabeling, immunoprecipitation, and SDS-PAGE fractionation of 2-5A binding proteins under denaturing conditions. Detection of a 2-5A binding protein at an apparent molecular weight of about 37 kDa, but not 80 kDa, coincided with severe CFS, while the presence of both bands corresponded with less severe CFS symptoms.

EXAMPLE 1

Identification of CFS Marker Molecule by Azido Photoaffinity Labelling and Immunoprecipitation Under Denaturing Conditions A. Study subjects and controls Study subjects were individuals who had previously been diagnosed as fulfilling the diagnostic criteria for CFS per the Centers for Disease Control and Prevention (CDC) guidelines of 1988 (Holmes et al., Ann.

Intern. Med. 108:387–389, 1988) and healthy controls. Patients and controls were selected from medical practices in Nevada and North Carolina. Criteria for selection of patients and controls and clinical variables at initiation of the study were as described by Suhadolnik et al., *Clin. Infect. Dis.* 18:S96-S104 (1994). At the time of blood sampling, selected symptoms were evaluated on a self-graded symptom checklist. Level of fatigue was assessed using the Karnofsky Performance Score (KPS) (mean KPS =56). Ten age- and gender-matched control subjects were recruited. Each CFS patient and healthy control underwent a medical history and physical examination. The age distribution of the controls was not significantly different from those of the individuals with CFS (CFS mean age=46 years; control mean age=41.7 years). All controls were interviewed and specifically denied having chronic fatigue or any other significant symptoms; the results of physical examinations were normal.

Approval for the study was obtained from local Institutional Review Boards. Informed consent was obtained from each patient and control. Peripheral blood mononuclear cells (PBMC) were separated from heparinized blood (50 ml) by Ficoll-Hypaque density gradient centrifugation and cytoplasmic extracts were prepared as previously described by Suhadolnik et al., *Biochemistry* 22:4153–4158 (1983), the entire disclosure of which is incorporated herein by reference. Cytoplasmic extracts were prepared without the addition of protease inhibitors.

B. Production of recombinant, human RNase L polyclonal antibody

Full-length human RNase L cDNA is described by Zhou et al., *Cell* 72:753–765 (1993), the entire disclosure of which is incorporated herein by reference, and contained as GenBank accession number L10381, also incorporated herein by reference. The glutathione S-transferase (GST) fusion protein strategy was used to obtain purified recombinant, human 80 kDa RNase L required for production of the RNase L polyclonal antibody. GST-RNase L fusion protein was obtained by expression in *E. coli* according to the procedure described by Sobol et al., *J. Biol. Chem.* 270:5963–5978 (1995), the entire disclosure of which is incorporated herein by reference. A polyclonal antibody against recombinant, human 80 kDa RNase L was elicited in New Zealand white rabbits by immunization with the highly purified recombinant, human GST-RNase L fusion protein. Serum was prepared before immunization and retained as a control (pre-immune serum). Initial inoculation was performed on day 1 with 100 µg of GST-RNase L mixed with an equal volume of complete Freund's adjuvant. Boosts with 50 µg of GST-RNase L (50% native and 50% heat denatured protein) mixed with incomplete Freund's adjuvant were given at 14, 21, 49 and 84 days. Blood samples for antibody production were drawn at 120, 150, and 180 days, preceded by additional boosts. Following hydrolysis of GST-RNase L fusion protein with human thrombin, RNase L was covalently coupled to the glutaraldehyde activated cartridge (Whatman) according to the manufacturer's specifications. Sodium borohydride was circulated through the column to reduce the glutaraldehyde that was not coupled to RNase L. The rabbit antiserum containing polyclonal antibody to RNase L was circulated through the glutaraldehyde column for 1 hour at room temperature and eluted according to the manufacturer's specifications. The RNase L polyclonal antibody was characterized by Western blotting using extracts of human 293 cells (ATCC CRL 1573) and an *E. coli* expressed recombinant GST-RNase L fusion protein, as described by Sobol et al., supra.

C. Azido photoaffinity labeling and immunoprecipitation of 2-5A binding proteins in PBMC extracts under denaturing conditions Chemical synthesis of the 2-5A azido photoprobe, ApAp (8-azidoA), 5'-monophosphorylation with [$\gamma$-$^{32}$P]ATP and polynucleotide kinase to produce [$^{32}$P]pApAp(8-azidoA) and photolabeling of 2-5A binding proteins in PBMC extracts were as described by Charubala et al., *Helv. Chim. Acta* 72:1354–1361 (1989), the entire disclosure of which is incorporated herein by reference. Photolabeling of the 2-5A binding proteins was thus accomplished by incubation of PBMC extracts (100 µg protein), prepared in the absence of added protease inhibitors, with the 2-5A photoprobe [$^{32}$P] pApAp(8-azidoA) (60 µCi/nmole, 5 µCi) (30 min, 4° C.), followed by UV irradiation (8000 watts/cm$^2$, 30 seconds, 0° C.). The photolabeling mixture was combined with affinity-purified RNase L polyclonal antibody (24 jig protein), Protein A-Sepharose (30 µl) and 100 µl phosphate-buffered saline (PBS), and the mixture was rotated for 1 hr at 4° C. After three PBS washes, the resin was mixed with 40 µl of protein solubilization solution, boiled for 5 minutes and centrifuged (10,600×g, 5 min., room temperature). The supernatant was fractionated by 10% SDS-PAGE. The azido-photolabeled/immunoprecipitated 2-5A binding proteins were visualized by autoradiography of the dried gel. The combined azido photolabeling/immunoprecipitation methodology eliminates proteins which immunoreact with the polyclonal antibody to RNase L, but are not 2-5A binding proteins, and also eliminates 2-5A binding proteins which are not immunoreactive to the polyclonal antibody to RNase L.

D. Results

Under the denaturing conditions of this experiment, three 2-5A binding proteins with molecular masses of 80, 42 and 37 kDa were observed in healthy control PBMC (FIG. 1, lanes 2,3) and in a subset of CFS PBMC (FIG. 1, lanes 1,4,5). However, photoaffinity labeling/immunoprecipitation revealed a second subset of CFS PBMC in which only one 2-5A binding protein with an estimated molecular mass of 37 kDa was observed; no 80 or 42 kDa 2- 5A binding proteins were observed (FIG. 1, lanes 6,7,8,9). The patients represented by lanes 1, 4 and 5 were characterized by less severe CFS symptoms. The patients represented by lanes 6, 7, 8 and 9 were characterized by more severe CFS symptoms. Thus, the assay results correlate with the severity of CFS presentation in the patients in the study.

The about 37 kDa 2-5A binding protein does not arise from protease-mediated degradation of the about 80 kDa RNase L at the time of PBMC extract preparation and processing. Quantitation by phosphorimager analysis demonstrated that the protein bands observed at 37 kDa in extracts of CFS PBMC were of equal intensity in the presence and absence of protease inhibitors, indicating that the about 37 kDa protein is stable.

EXAMPLE 2

Identification of CFS Marker Molecule by Azido Photoaffinity Labelling and Assay of 2-5A Dependent RNase L Enzyme Activity Under Native (non-denaturing) Conditions A. Molecular mass estimation of 2-5A binding proteins in PBMC extracts by analytical gel permeation HPLC under native conditions Extracts of PBMC (200 μg protein) from individuals with CFS or healthy controls were incubated for 30 min. at 4° C. in the presence of [$^{32}$P]pApAp(8-azidoA) (109 μCi/nmole, 10 μCi), uv irradiated (8000 watts/cm$^2$, 30 sec., 0° C.), loaded onto a Superdex 200 (Hiload 16/60) gel filtration column (Pharmacia Biotech Inc.) and eluted at room temperature with 25 mM Tris-Cl (pH 7.4), 80 mM KCl, 1 mM EDTA, 5 mM MgCl$_2$, 0.1 mM ATP, and 14 mM β-mercaptoethanol at a flow rate of 0.5 ml/min; 0.5 ml fractions were collected. The [$^{32}$P]azido 2-5A photoprobe that was covalently linked to the 2-5A binding protein(s) in each fraction was quantitated by Cerenkov radiation (50% efficiency) scintillation spectrometry in a Tm Analytics model 6895 scintillation spectrometer. The Superdex 200 column was calibrated with myosin, β-galactosidase, phosphorylase b, bovine serum albumin, ovalbumin, carbonic anhydrase, and soybean trypsin inhibitor (220, 116, 97.4, 68, 44, 31, and 21.5 kDa, respectively).

B. 2-5A dependent RNase L enzyme activity in PBMC extracts following analytical gel permeation HPLC under native conditions Extracts of PBMC (200 μg protein) from healthy controls and individuals with CFS were fractionated under native conditions on a Superdex 200 gel filtration column as described in the previous paragraph. RNase L activity in an aliquot (5–20 μl) of each fraction was determined by the hydrolysis of poly(U)-3'-[$^{32}$P]pCp (20,000 dpm) in reaction mixtures (15–30 μl) containing p$_3$A$_3$ (1×10$^{-8}$ M to 1×10$^{-7}$ M) (Sobol et al., supra). The determination of non-specific RNase activity was measured by hydrolysis of poly(C)-3'-[$^{32}$P]pCp (14,000 dpm) in reaction mixtures (15–30 μl) in the absence of p$_3$A$_3$. Radioactive measurements were accomplished using Scintiverse I (Fisher) (>99% efficiency).

C. Results

In healthy control PBMC extracts analyzed under native conditions, 2-5A binding and 2-5A dependent RNase L enzyme activity were observed at 80 and 42 kDa (FIGS. 2A and 2D). In one subset of CFS PBMC extracts, three 2-5A binding proteins with 2-5A dependent RNase L enzyme activity were observed. In this subset, 2-5A binding proteins with 2-5A dependent RNase L enzyme activity were observed either at 80, 42 and 30 kDa (FIGS. 2B and 2E) or at 80, 42 and 30 kDa. In a second subset of CFS PBMC extracts (as shown in FIG. 1, lanes 6,7,8,9), no 2-5A binding or 2-5A dependent RNase L enzyme activity was observed at 80 or 42 kDa; however, 2-5A binding and 2-5A dependent RNase L enzyme activity was observed at 30 kDa (FIGS. 2C and 2F). Poly(C)-3'-[$^{32}$P]pCp was used in control assays to show that the 2-5A dependent RNase L enzyme activity observed in PBMC extracts was not due to non-specific RNase activity. No hydrolysis of poly(C)-3'-[$^{32}$P]pCp was observed in any fraction and is taken as additional evidence for the presence of 2-5A dependent RNase L. Specificity of the [$^{32}$P]pApAp-(8-azidoA) photoprobe was confirmed by competition experiments with authentic p$_3$A$_3$ (data not shown). Furthermore, no hydrolysis of poly(U)-3'-[$^{32}$P]pCp was observed in the absence of 2-5A, the allosteric activator of RNase L.

The 2-5A binding protein observed at 37 kDa under denaturing conditions upon SDS-PAGE analysis is in reasonable agreement with the 30 kDa protein observed under native conditions, based on literature precedents accounting for differences in molecular mass observed under denaturing and native conditions (Somerville et al., *J. Bacteriol.* 117:3837–3842, 1995).

EXAMPLE 3

Stability of Immunoreactive 2-5A Binding Proteins to Proteolysis

PBMC extracts were prepared in the presence and absence of protease inhibitors to assess the possible effect of proteolytic degradation during the preparation and processing of the extracts. Preparation of cytoplasmic extracts in the presence of protease inhibitor was according to the manufacturer's directions (Mini-Complete™ protease inhibitor cocktail tablets, Boehringer/Mannheim, containing aprotinin, leupeptin, pefabloc®SC and EDTA). Suhadolnik et al., *Clin. Infect. Dis.*, supra. The azido photoprobe, [$^{32}$P]pApAp(8-azidoA), was covalently bound to its 2-5A binding proteins and further purified by immunoprecipitation with recombinant, human 80 kDa RNase L polyclonal antibody. The photoaffinity labeled, immunoreactive 2-5A binding proteins were quantitated by phosphorimager analysis after SDS-PAGE. CFS PBMC extract prepared in the presence of protease inhibitors contained a low molecular weight imnnunoreactive 2-5A binding protein at 37 kDa in addition to the 80 kDa 2-5A dependent RNase L (FIG. 3, lane 1). Photoaffinity labeling and immunoprecipitation of the same CFS PBMC extract, prepared in the absence of protease inhibitors, revealed immunoreactive 2-5A binding proteins at 37 and 42 kDa in addition to the 80 kDa RNase L (FIG. 3, lane 2). Quantitation by phosphorimager analysis demonstrated that the protein bands observed at 37 kDa in extracts of CFS PBMC were of equal intensity in the presence and absence of protease inhibitors, indicating that the 37 kDa protein is stable (FIG. 3, lanes 1 and 2). In extracts of healthy control PBMC prepared in the presence of protease inhibitors, only the 80 kDa RNase L was detected (FIG. 3, lane 3). In the same extract prepared in absence of protease inhibitors, there was a 70% decrease in the 80 kDa RNase L (FIG. 3, compare lanes 3 and 4). However, no 37 kDa immunoreactive 2-5A binding protein was detected in this healthy control PBMC extract prepared in the presence or absence of protease inhibitors (FIG. 3, lanes 3 and 4). In a few healthy control PBMC extracts tested, an immunoreactive 2-5A binding protein was observed at 50 kDa, but not at 37 kDa (FIG. 3, lane 4). However, the 50 kDa 2-5A binding protein did not exhibit 2-5A dependent RNase L activity as measured by the hydrolysis of poly(U)-3'-[$^{32}$P]pCp (data not shown).

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indication the scope of the invention.

What is claimed is:

1. A method for diagnosing chronic fatigue syndrome comprising:

(a) contacting a patient sample with a probe compound comprising a compound according to formula I bearing a detectable label, under conditions sufficient to form covalent conjugates of said probe compound and 2',5'-oligoadenylate-binding proteins in the sample:

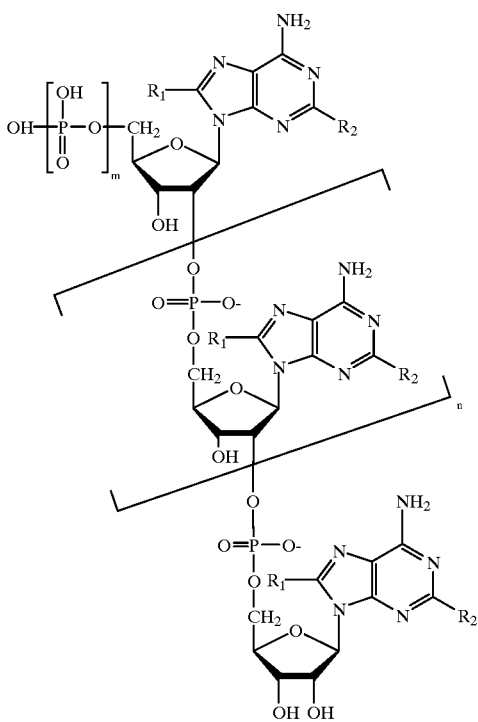

wherein
m is an integer from 0 to 3,
n is an integer from 1 to 3, and
each $R_1$ and each $R_2$ is independently selected from the group consisting of hydrogen and $N_3$, provided at least one of $R_1$ or one of $R_2$ is $N_3$, or a water soluble salt of said compound;
(b) contacting the sample containing said covalent conjugates with an antibody which binds RNase L species in the sample;
(c) separating the proteins in said sample by gel electrophoresis; and
(d) examining said proteins separated by said gel electrophoresis for the presence of proteins of about 37 kDa apparent molecular weight according to sodium dodecyl sulfate-polyacrylamide gel electrophoresis, which proteins
(i) have formed a covalent conjugate with the probe compound, and
(ii) are bound by said antibody;
the presence of said about 37 kDa apparent molecular weight proteins which have formed covalent conjugates with the probe compound and which are bound by said antibody being diagnostic for chronic fatigue syndrome.

2. A method according to claim 1 wherein the conditions for forming said covalent conjugates include ultraviolet irradiation of said sample to covalently bond said probe compound to the 2',5'-oligoadenylate-binding proteins in the sample.

3. A method according to claim 2, wherein n is 1 in the probe compound.

4. A method according to claim 3, wherein m is 1 in the probe compound.

5. A method according to claim 4 wherein each $R_2$ in the probe compound is hydrogen.

6. A method according to claim 5 wherein the probe compound is 5'-O-phosphoryl-adenylyl-(2'→5')-adenylyl-(2'→5')-8-azidoadenosine, or salt thereof.

7. A method according to claim 2 wherein the sample comprises blood or a fraction thereof.

8. A method according to claim 7 wherein the sample comprises a cytoplasmic extract of peripheral blood mononuclear cells.

9. A method according to claim 2 wherein the detectable label on said probe compound is a radiolabel.

10. A method according to claim 9 wherein the radiolabel is a $^{32}P$ atom.

11. A method according to claim 1 wherein the conditions for forming said covalent conjugates include ultraviolet irradiation of said sample to covalently bond said probe compound to the 2',5'-oligoadenylate-binding proteins in the sample.

12. A method according to claim 11 wherein n is 1 in the probe compound.

13. A method according to claim 12 wherein m is 1 in the probe compound.

14. A method according to claim 13 wherein each $R_2$ in the probe compound is hydrogen.

15. A method according to claim 14 where in the probe compound is 5'-O-phosphoryl-adenylyl-(2'→5')-adenylyl-(2'→5')-8-azidoadenosine, or salt thereof.

16. A method according to claim 1 wherein protease inhibitor is added to the sample to inhibit the activity of proteases which may be present in the sample.

17. A method for detecting severe chronic fatigue syndrome comprising:
(a) contacting a patient sample with a probe compound comprising a compound according to formula I bearing a detectable label, under conditions sufficient to form covalent conjugates of said probe compound and 2',5'-oligoadenylate-binding proteins in the sample:

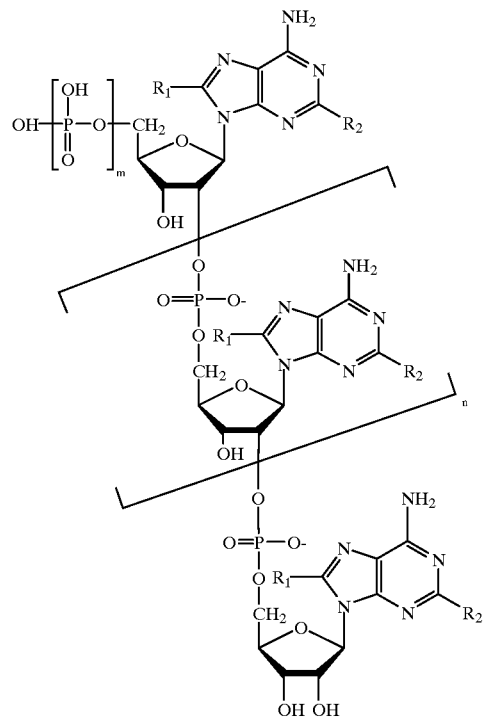

wherein
m is an integer from 0 to 3,
n is an integer from 1 to 3, and
each $R_1$ and each $R_2$ is independently selected from the group consisting of hydrogen and $N_3$, provided at least one of $R_1$ or one of $R_2$ is $N_3$, or a water soluble salt of said compound;

(b) contacting the sample containing said covalent conjugates with an antibody which binds RNase L species in the sample;

(c) separating the proteins in said sample by gel electrophoresis; and (d) examining said proteins separated by said gel electrophoresis for the presence of proteins of about 37 kDa and about 80 kDa apparent molecular weight proteins according to sodium dodecyl sulfate-polyacrylamide gel electrophoresis, which about 37 kDa and 80 kDa proteins (i) have formed a covalent conjugate with the probe compound, and (ii) are bound by said antibody;

the presence of about 37 kDa apparent molecular weight proteins which have formed covalent conjugates with the probe compound and which are bound by said antibody, and the absence of about 80 kDa apparent molecular weight proteins which have formed covalent conjugates with the probe compound and which are bound by said antibody, being diagnostic for severe chronic fatigue syndrome.

* * * * *

UNITED STATES PATENT AND TRADEMARK OFFICE
CERTIFICATE OF CORRECTION

PATENT NO.        : 6,214,554 B1
APPLICATION NO.   : 09/296211
DATED             : April 10, 2001
INVENTOR(S)       : Robert J. Suhadolnik Page 1 of 1

It is certified that error appears in the above-identified patent and that said Letters Patent is hereby corrected as shown below:

Column 1, lines 13-16, cancel the text and insert the following:

--This invention was made with government support under grant R21 AI38378 awarded by the United States Public Health Service. The government has certain rights in the invention.--

Signed and Sealed this

Eleventh Day of October, 2011

David J. Kappos
*Director of the United States Patent and Trademark Office*